US012745916B2

(12) United States Patent
Zhao et al.

(10) Patent No.: US 12,745,916 B2
(45) Date of Patent: Sep. 29, 2026

(54) OPTICAL SIGNAL PROCESSING METHOD AND SYSTEM, ELECTRONIC DEVICE

(71) Applicant: KINGFAR INTERNATIONAL INC., Beijing (CN)

(72) Inventors: Qichao Zhao, Beijing (CN); Ran Yang, Beijing (CN); Qingju Wang, Beijing (CN)

(73) Assignee: KINGFAR INTERNATIONAL INC., Beijing (CN)

( * ) Notice: Subject to any disclaimer, the term of this patent is extended or adjusted under 35 U.S.C. 154(b) by 0 days.

(21) Appl. No.: 18/938,442

(22) Filed: Nov. 6, 2024

(65) Prior Publication Data

US 2025/0064330 A1 Feb. 27, 2025

Related U.S. Application Data

(63) Continuation of application No. PCT/CN2023/141139, filed on Dec. 22, 2023.

(30) Foreign Application Priority Data

Dec. 27, 2022 (CN) ......................... 202211682738.1
Dec. 27, 2022 (CN) ......................... 202211686554.2

(51) Int. Cl.
*A61B 5/021* (2006.01)
*A61B 5/00* (2006.01)
*A61B 5/024* (2006.01)

(52) U.S. Cl.
CPC ...... *A61B 5/02116* (2013.01); *A61B 5/02416* (2013.01); *A61B 5/725* (2013.01)

(58) Field of Classification Search
CPC ............ A61B 5/02116; A61B 5/02416; A61B 5/14551; A61B 5/725; A61B 2560/0247; A61B 5/7203
See application file for complete search history.

(56) References Cited

U.S. PATENT DOCUMENTS 5,846,190 A * 12/1998 Woehrle ............... A61B 5/6843 600/336
6,343,177 B1 * 1/2002 Estoque ............... A61B 5/6838 385/74

(Continued)

FOREIGN PATENT DOCUMENTS

CN 106773616 A 5/2017
CN 111493850 A 8/2020

(Continued)

OTHER PUBLICATIONS

International Search Report received in corresponding International Patent Application No. PCT/CN2023/141139, mailed Mar. 26, 2024, 9 pages.

(Continued)

*Primary Examiner* — Oommen Jacob
(74) *Attorney, Agent, or Firm* — Cooper Legal Group, LLC

(57) ABSTRACT

A system, an electronic device and an optical signal processing method including receiving optical signals by a spectrum analyzer, which outputs a first wavelength range of the optical signals, primary filtering the first wavelength range based on a pre-set wavelength threshold of red light to obtain a second wavelength range, accessing wavelength ranges of ambient light acquired, respectively accessing upper limit values and lower limit values of the wavelength ranges of the ambient light, obtaining a filtering upper and lower limit value respectively based on the upper limit values and the lower limit values, and setting a filtering wavelength range based on the filtering upper limit value and the filtering lower limit value, re-filtering the second wavelength range based on the filtering wavelength range to obtain a target filtering range, filtering the optical signals (Continued)

with the target filtering range to filter out ambient light from the optical signals.

14 Claims, 3 Drawing Sheets

(56) References Cited

U.S. PATENT DOCUMENTS

| | | | | |
|---|---|---|---|---|
| 6,616,613 | B1 | 9/2003 | Goodman | |
| 7,003,339 | B2 * | 2/2006 | Diab | A61B 5/14552 600/336 |
| 7,611,064 | B2 * | 11/2009 | Zhu | G06F 9/44526 235/472.01 |
| 7,972,266 | B2 * | 7/2011 | Gobeyn | A61B 5/445 348/222.1 |
| 8,204,567 | B2 * | 6/2012 | Petersen | A61B 5/7203 600/323 |
| 8,315,684 | B2 * | 11/2012 | Petersen | A61B 5/7228 600/336 |
| 9,265,456 | B2 * | 2/2016 | Kirenko | A61B 5/14551 |
| 10,015,859 | B2 * | 7/2018 | Dong | H05B 45/20 |
| 2008/0208021 | A1 * | 8/2008 | Cinbis | A61B 5/361 600/324 |
| 2009/0326347 | A1 * | 12/2009 | Scharf | A61B 5/14552 600/323 |
| 2010/0217102 | A1 * | 8/2010 | LeBoeuf | A61B 5/7282 600/310 |
| 2010/0324384 | A1 * | 12/2010 | Moon | A61B 5/14552 600/595 |
| 2012/0113412 | A1 * | 5/2012 | Kawamata | G01J 1/4204 356/51 |
| 2012/0197093 | A1 * | 8/2012 | LeBoeuf | A61B 5/7203 250/226 |
| 2012/0197137 | A1 * | 8/2012 | Jeanne | A61B 5/0261 600/479 |
| 2013/0060098 | A1 * | 3/2013 | Thomsen | A61B 5/0816 600/479 |
| 2013/0296665 | A1 * | 11/2013 | Kassim | A61B 5/0295 600/310 |
| 2013/0296666 | A1 * | 11/2013 | Kumar | A61B 5/02416 600/310 |
| 2014/0022535 | A1 * | 1/2014 | Yamamoto | G01J 3/021 356/402 |
| 2014/0347324 | A1 * | 11/2014 | Wu | G06F 3/0304 345/175 |
| 2015/0036138 | A1 * | 2/2015 | Watson | G01N 21/65 356/402 |
| 2015/0148632 | A1 * | 5/2015 | Benaron | A61B 5/0059 600/476 |
| 2015/0236740 | A1 * | 8/2015 | De Haan | A61B 5/7246 375/340 |
| 2016/0066863 | A1 * | 3/2016 | Thaveeprungsriporn | A61B 5/7278 600/323 |
| 2017/0042435 | A1 * | 2/2017 | Vermeulen | A61B 5/7203 |
| 2017/0086690 | A1 * | 3/2017 | Freschl | A61B 5/08 |
| 2017/0188864 | A1 * | 7/2017 | Drury | A61B 5/02427 |
| 2017/0238805 | A1 * | 8/2017 | Addison | A61B 5/1032 |
| 2017/0367580 | A1 * | 12/2017 | DiMaio | A61B 5/445 |
| 2018/0317875 | A1 * | 11/2018 | Khayrullaev | A61B 5/7221 |
| 2019/0175042 | A1 * | 6/2019 | Wang | A61B 5/352 |
| 2019/0175116 | A1 * | 6/2019 | Wijshoff | A61B 5/02416 |
| 2019/0183364 | A1 * | 6/2019 | Basu | A61B 5/6826 |
| 2022/0160308 | A1 * | 5/2022 | Chang | A61B 5/7246 |
| 2025/0064330 | A1 * | 2/2025 | Zhao | A61B 5/7203 |

FOREIGN PATENT DOCUMENTS

| | | | |
|---|---|---|---|
| CN | 113116321 | A | 7/2021 |
| CN | 114052688 | A | 2/2022 |
| CN | 115299898 | A | 11/2022 |
| CN | 116028809 | A | 4/2023 |
| CN | 116592998 | A | 8/2023 |

OTHER PUBLICATIONS

First Office Action received in corresponding Chinese patent application No. 202211686554.2, dated Sep. 5, 2023, 12 pages.

Second Office Action received in corresponding Chinese patent application No. 202211686554.2, dated Nov. 20, 2023, 12 pages.

* cited by examiner

OPTICAL SIGNAL PROCESSING METHOD AND SYSTEM, ELECTRONIC DEVICE

CROSS-REFERENCE TO RELATED APPLICATION

The present disclosure is a continuation of PCT application serial no. PCT/CN2023/141139, filed on Dec. 22, 2023, which claims priority to Chinese patent application No. 202211682738.1, entitled "Method and System for Filtering Out Interference of Ambient Light in Optical Signal Acquisition Process", filed on Dec. 27, 2022 with CNIPA, and to Chinese Patent Application No. 202211686554.2, entitled "Measurement Model Training and Measurement Method and Apparatus for Continuous Blood Pressure", filed on Dec. 27, 2022 with CNIPA. The entireties of PCT application serial no. PCT/CN2023/141139, Chinese patent application No. 202211682738.1, and Chinese Patent Application No. 202211686554.2 are hereby incorporated by reference herein and made a part of this specification.

TECHNICAL FIELD

The present disclosure relates to the technical field of optical signal processing, and in particular, to an optical signal processing method and system, a continuous blood pressure measurement method, and an electronic device.

BACKGROUND ART

In the prior art, functional near-infrared spectroscopy (fNIRS) may detect functional brain activity, which provides hemodynamic information on the basis of the changes of hemoglobin concentration, reflects the blood oxygen metabolism status of cerebral cortex, and has the characteristics of high time resolution and being easy to use. In addition, photo-plethysmography (PPG) based on infrared light may be used to detect the pulse wave of people with high incidence of cardiovascular disease in the early stage. Countermeasures may be taken in the early stage when finding out an abnormality, which is of great significance to prevent and delay the occurrence and development of cardiovascular disease. Photo-plethysmography may be used not only for the measurement of vascular pulse but also for continuous blood pressure measurement. By means of the continuous blood pressure monitoring, blood pressure abnormalities may be detected timely and it is more effective than intermittent blood pressure monitoring in detecting, controlling and treating hemodynamic disease.

However, the interference of ambient light has a great impact on the detection results either by fNIRS or by PPG technology. At present, most of the near-infrared data acquisition or infrared data acquisition is basically achieved by way of shading or through filters to record data accurately, but a small amount of near-infrared light will enter the system to affect the accurate acquisition of near-infrared or infrared data.

In addition, in the existing blood pressure acquisition apparatus for measuring the continuous blood pressure value by analyzing the acquired photo-plethysmography signal, the method for measuring continuous blood pressure value may not accurately measure the continuous blood pressure values due to the error of the signals acquired by the acquisition apparatus for photo-plethysmography signal, the insufficiently detailed and accurate analysis method and no calibration.

Therefore, how to improve the accuracy of signal detection results is a problem to be solved.

SUMMARY OF THE INVENTION

In view of the foregoing, embodiments of the present disclosure provide an optical signal processing method and system, a continuous blood pressure measurement method, and an electronic device to obviate or ameliorate one or more disadvantages of the prior art.

In one respect, the present disclosure provides an optical signal processing method including:

receiving optical signals to be processed by a spectrum analyzer, and outputting a first wavelength range of the optical signal to be processed by the spectrum analyzer, primary filtering the first wavelength range based on a pre-set wavelength threshold of red light to obtain a second wavelength range, accessing wavelength ranges of a plurality of groups of ambient light acquired in advance, respectively accessing a plurality of upper limit values and a plurality of lower limit values of the wavelength ranges of the plurality of groups of ambient light, obtaining a filtering upper limit value based of the plurality of upper limit values, obtaining a filtering lower limit value based on the plurality of lower limit values, and setting a filtering wavelength range based on the filtering upper limit value and the filtering lower limit value, re-filtering the second wavelength range based on the filtering wavelength range to obtain a target filtering range, filtering the optical signals to be processed with the target filtering range to filter out ambient light from the optical signals to be processed.

By the above-mentioned solution, the wavelength of red light is used to perform the primary filtering on the optical signals to be processed, then it is re-filtered through the plurality of groups of ambient light acquired in advance, so as to obtain the target filtering wavelength range of the ambient light to be filtered out, then the target filtering range is filtered out from the optical signals to be processed by the filter, so as to filter out the ambient light from the optical signals to be processed. Compared with the traditional method by means of shading or through a filter, the ambient light may be more accurately filtered out with the present method, thereby achieving a more accurate optical signal collection.

In some embodiments of the present disclosure, a step of primary filtering the first wavelength range based on a pre-set wavelength threshold of red light to obtain a second wavelength range includes: obtaining a wavelength range of red light, a lower limit value of the wavelength range of red light is defined as a wavelength threshold of red light, and filtering out wavelength ranges higher than the wavelength threshold of red light from the first wavelength range to obtain a second wavelength range, and/or, the wavelength ranges of the plurality of groups of ambient light includes wavelength ranges of ambient light acquired from a dark environment, wavelength ranges of ambient light acquired from outdoor, and wavelength ranges of ambient light acquired from indoor.

In some embodiments of the present disclosure, a step of obtaining a filtering upper limit value based of the plurality of upper limit values, obtaining a filtering lower limit value based on the plurality of lower limit values includes: respectively acquiring weighting parameters corresponding to the wavelength ranges of the plurality of groups of ambient light, respectively calculating a weighted average value of the plurality of upper limit values and a weighted average value of the plurality of lower limit values based on the weighting parameters to obtain the filtering upper limit value and the filtering lower limit value; or defining a minimum lower limit value among the plurality of lower limit values as the filtering lower limit value, and a maximum upper limit value among the plurality of upper limit values as the filtering upper limit value.

In some embodiments of the present disclosure, a step of re-filtering the second wavelength range based on the filtering wavelength range to obtain a target filtering range includes: accessing a wavelength range belonging to the filtering wavelength range from the second wavelength range as the target filtering range.

In some embodiments of the present disclosure, a step of filtering the optical signal to be processed with the target filtering range to filter out ambient light from the optical signals to be processed includes: filtering the optical signals to be processed with the target filtering range, and filtering out optical signals with a wavelength range being the target filtering range from the optical signals to be processed.

According to some embodiments of the present disclosure, the method further includes:

- acquiring photo-plethysmography signal data from the optical signals to be processed after filtering out ambient light,
- inputting the photo-plethysmography signal data into a pre-trained continuous blood pressure measurement model to obtain continuous blood pressure values, the pre-trained continuous blood pressure measurement model is obtained by a training based on following steps:
- acquiring the photo-plethysmography signal data from the signals to be processed after filtering out ambient light and normal arterial blood pressure waveform data,
- processing the photo-plethysmography signal data and the normal arterial blood pressure waveform data according to a pre-set data processing method to obtain a training sample, and
- performing the training using the training sample based on a convolutional neural network to obtain the continuous blood pressure measurement model.

Another aspect of the present disclosure provides a continuous blood pressure measurement method, including:

- filtering out ambient light from optical signals to be processed, and acquiring photo-plethysmography signal data from the optical signals to be processed after filtering out ambient light,
- inputting the photo-plethysmography signal data into a pre-trained continuous blood pressure measurement model to obtain continuous blood pressure values, the pre-trained continuous blood pressure measurement model is obtained by a training based on following steps:
- acquiring the photo-plethysmography signal data from the signals to be processed after filtering out ambient light and normal arterial blood pressure waveform data,
- processing the photo-plethysmography signal data and the normal arterial blood pressure waveform data according to a pre-set data processing method to obtain a training sample, and
- performing the training using the training sample based on a convolutional neural network to obtain the continuous blood pressure measurement model.

In some embodiments of the present disclosure, the continuous blood pressure acquisition apparatus includes at least one eight-channel light source for main light source projection and at least one photosensitive diode for receiving data from a multi-channel light source.

In some embodiments of the present disclosure, a standard deviation is calculated according to the continuous blood pressure values and a standard blood pressure value, the standard blood pressure value is an average value of a plurality of blood pressure measurement values; and a blood pressure measurement is repeated if the standard deviation is greater than a standard deviation threshold.

In some embodiments of the present disclosure, a step of processing the photo-plethysmography signal data and the normal arterial blood pressure waveform data according to a pre-set data processing method to obtain a training sample includes:

- deleting photo-plethysmography signal data and normal arterial blood pressure waveform data that are less than a length threshold,
- filtering out photo-plethysmography signal data and normal arterial blood pressure waveform data that are not within a pre-set frequency band with a Butterworth bandpass filter,
- filtering the photo-plethysmography signal data and the normal arterial blood pressure waveform data with a Hampel filter to remove outliers,
- dividing the photo-plethysmography signal data and the normal arterial blood pressure waveform data in cycles, and deleting flat lines or flat peaks in the cycles, and
- deleting a cycle with a ratio of flat lines and flat peaks greater than a ratio threshold.

In some embodiments of the present disclosure, a step of processing the photo-plethysmography signal data and the normal arterial blood pressure waveform data according to a pre-set data processing method to obtain a training sample further includes: intercepting two corresponding short segments of normal arterial blood pressure waveform in proximity to the cycles of the photo-plethysmography signal data, and calculating an average peak value of peak values and an average valley value of valley values in the two short segments of normal arterial blood pressure waveform, by which the average peak value is defined as a systolic blood pressure, the average valley value is defined as a diastolic blood pressure, and the systolic blood pressure and the diastolic blood pressure are defined as labels of the training sample.

Another aspect of the present disclosure provides an optical signal processing system configured to be applied to the method of the present disclosure including:

- an optical signal receiving module configured to access optical signals to be processed through a spectrum analyzer, the spectrum analyzer outputs a first wavelength range of the optical signals to be processed,
- a primary filter module configured to primarily filter the first wavelength range based on a pre-set wavelength threshold of red light to obtain a second wavelength range,
- a calculation module of filtration configured to acquire wavelength ranges of a plurality of groups of ambient light acquired in advance, to respectively acquire a plurality of upper limit values and a plurality of lower limit values of the wavelength ranges of the plurality of groups of ambient light, to obtain a filtering upper limit value based on the plurality of upper limit values and a filtering lower limit value based on the plurality of lower limit values, and to set a filtering wavelength range based on the filtering upper limit value and the filtering lower limit value, a re-filter module configured to re-filter the second wavelength range based on the filtering wavelength range to obtain a target filtering range, and an ambient light filtering out module configured to filter the optical signals to be processed with the target filtering range to filter out ambient light from the optical signals to be processed.

Another aspect of the present disclosure also provides an electronic device including a memory and a processor, a computer program is stored in the memory, and the processor is configured to implement the optical signal processing method as described above or the continuous blood pressure measurement method as described above when executing the computer program.

Another aspect of the present disclosure further provides a computer-readable storage medium storing a computer program which, when executed by a processor, implements the optical signal processing method as described above or the continuous blood pressure measurement method as described above.

The present disclosure enables a continuous blood pressure measurement and improves the accuracy and speed of the blood pressure measurement.

Additional advantages, objects, and features of the present disclosure will be set forth in part in the description which follows and in part will become apparent to a person skilled in the art upon studying of the following or may be learned from practice of the present disclosure. The purpose and other advantages of the present disclosure can be specifically pointed out and obtained in the specification and drawings.

It will be appreciated by a person skilled in the art that the objects and advantages which may be achieved with the present disclosure are not limited to those specifically described above, and that the foregoing and other objects which can be achieved with the present disclosure will be more clearly understood from the following detailed description.

BRIEF DESCRIPTION OF THE DRAWINGS

The accompanying drawings described herein are intended to provide a further understanding of the present disclosure, form a part of the present application, and are not intended to limit the present disclosure.

DETAILED DESCRIPTION OF THE INVENTION

Figure 1:
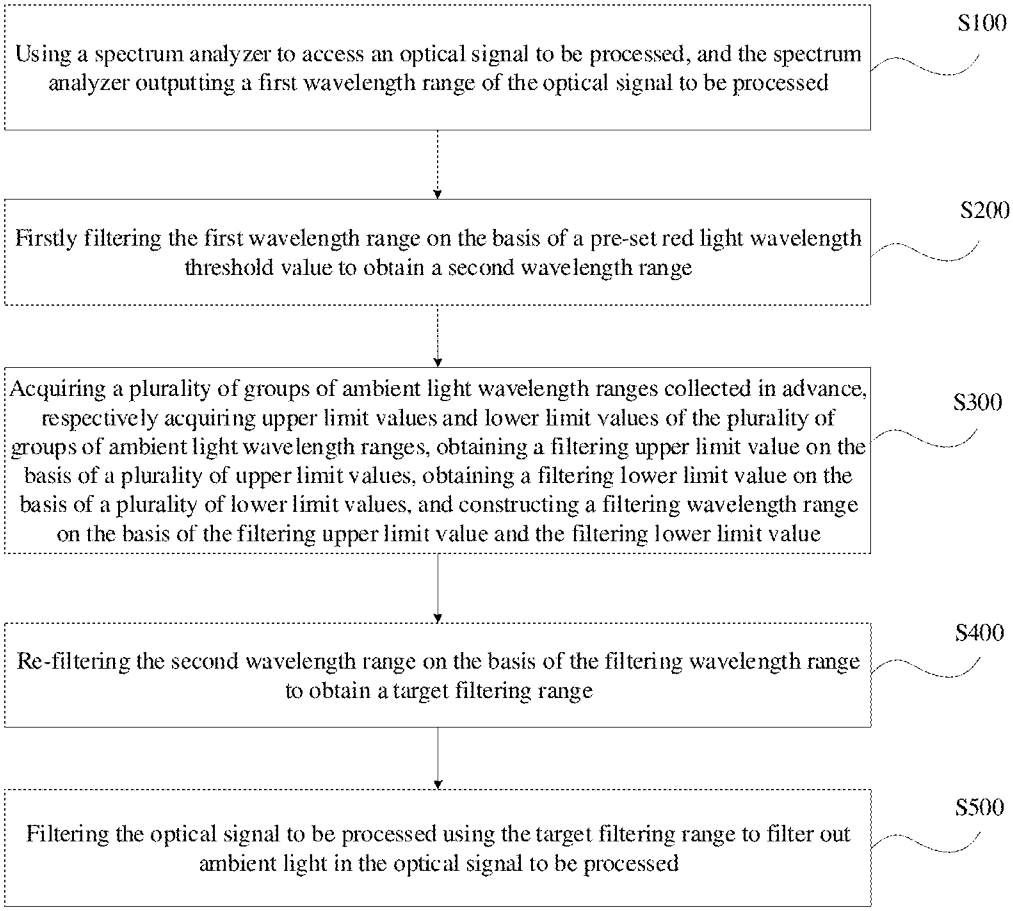
FIG. 1 is a schematic flowchart of an optical signal processing method according to an embodiment of the present disclosure.

In order that the objects, technical solutions and advantages of the present disclosure may be more clearly understood, the present disclosure will be described in further detail below in combination with the embodiments and accompany drawings. Illustrative embodiments of the disclosure and descriptions thereof are set forth herein to illustrate, but not to limit the disclosure.

It is also noted herein that, in order to avoid obscuring the present disclosure with unnecessary detail, only structures and/or process steps that are germane to the technical solution in accordance with the present disclosure are shown in the drawings, and other details that are not germane to the present disclosure are omitted.

It should be emphasized that the term "contain/include" when used herein is taken to specify the presence of stated features, elements, steps or components, but does not preclude the presence or addition of one or more other features, elements, steps or components.

It is also noted herein that, unless otherwise specified, the term "connected" may refer herein not only to a direct connection, but also to an indirect connection where an intermediate is present.

In the following text, embodiments of the present disclosure will be described with reference to the accompanying drawings. Throughout the drawings, the same reference numerals indicate the same or similar components or the same or similar steps.

In order to leach inference of ambient light during optical signal acquisition, the present disclosure provides an optical signal processing method, as shown in FIG. 1, including:

Step S100, receiving optical signals to be processed by a spectrum analyzer, and outputting a first wavelength range of the optical signals to be processed by the spectrum analyzer.

In some embodiments of the disclosure, the spectrum analyzer may be a classical spectrometer or a novel spectrometer.

Step S200, primary filtering the first wavelength range based on a pre-set wavelength threshold of red light to obtain a second wavelength range.

Step S300, accessing wavelength ranges of a plurality of groups of ambient light acquired in advance, respectively accessing a plurality of upper limit values and a plurality of lower limit values of the wavelength ranges of the plurality of groups of ambient light, obtaining a filtering upper limit value by means of a weighted calculation based on the plurality of upper limit values, obtaining a filtering lower limit value by means of a weighted calculation based on the plurality of lower limit values, and setting a filtering wavelength range based on the filtering upper limit value and the filtering lower limit value.

In some embodiments of the present disclosure, the plurality of groups of ambient light includes ambient light acquired from a dark environment, ambient light acquired from outdoor and ambient light acquired from indoor, the plurality of groups of ambient light correspond to a plurality of wavelength ranges. The spectrum analyzer may output the wavelength ranges of ambient light after acquiring the ambient light, and may obtain an upper limit value and a lower limit value of each of the wavelength ranges.

In the specific implementation, the wavelength range of the light measured in a dark box may be taken as the wavelength range of the ambient light acquired from a dark environment, the wavelength range of the ambient light acquired from outdoor and the wavelength range of the ambient light acquired from indoor may be wavelength ranges of ambient light directly measured from outdoor and indoor environments, respectively.

Step S400, re-filtering the second wavelength range based on the filtering wavelength range to obtain a target filtering range.

Step S500, filtering the optical signals to be processed with the target filtering range to filter out ambient light from the optical signals to be processed.

By the above-mentioned solution, the wavelength of red light is used to primary filter the wavelength of the optical signals to be processed, which is then re-filtered based on the wavelength ranges corresponding to the plurality of groups of ambient light acquired in advance, so as to obtain the target filtering wavelength range of ambient light to be filtered out, then the optical signals within the target filtering range are filtered out from the optical signals to be processed by the filter, so as to filter out ambient light from the optical signals to be processed. Compared with the traditional method by means of shading or through a filter, the ambient light may be more accurately filtered out with the present method, thereby achieving a more accurate optical signal acquisition.

In some embodiments of the present disclosure, the step of primary filtering the first wavelength range based on a pre-set wavelength threshold of red light to obtain a second wavelength range includes:

obtaining a wavelength range of red light, by which a lower limit value of the wavelength range of red light is defined as a wavelength threshold of red light; and filtering out wavelength ranges higher than the wavelength threshold of red light from the first wavelength range to obtain a second wavelength range.

In the specific implementations the wavelength range of red light may be from 625 nm to 740 nm.

Since the wavelength range of red light and the wavelength range of infrared light do not belong to the wavelength range of ambient light, the wavelength range higher than the wavelength threshold of red light may be accurately filtered out by the present solution.

In some embodiments of the present disclosure, in the step of accessing wavelength ranges of a plurality of groups of ambient light acquired in advance, respectively accessing a plurality of upper limit values and a plurality of lower limit values of the wavelength ranges of the plurality of groups of ambient light, if the wavelength ranges of the plurality of groups of ambient light include wavelength ranges of ambient light acquired from a dark environment, wavelength ranges of ambient light acquired from outdoor, and wavelength ranges of ambient light acquired from indoor, an upper limit value and a lower limit value of each wavelength range of ambient light acquired are respectively accessed.

In some embodiments of the present disclosure, in the step of obtaining a filtering upper limit value based of the plurality of upper limit values, obtaining a filtering lower limit value based on the plurality of lower limit values, if the wavelength ranges of the plurality of groups of ambient light include the wavelength ranges of ambient light acquired from dark environment, the wavelength ranges of ambient light acquired from outdoor and the wavelength ranges of ambient light acquired from indoor, weighting parameters corresponding to the wavelength ranges of ambient light acquired from dark environment, the wavelength ranges of ambient light acquired from outdoor and the wavelength range of ambient light acquired from indoor are respectively determined, a weighted average value of the plurality of upper limit values and that of the plurality of lower limit values are calculated based on the weighting parameters to obtain a filtering upper limit value and a filtering lower limit value.

In some embodiments of the present disclosure, in the step of a weighted average value of the plurality of upper limit values and that of the plurality of lower limit values are calculated based on the weighting parameters to obtain a filtering upper limit value and a filtering lower limit value, the filtering upper limit value and the filtering lower limit value are respectively calculated based on the following formula:

$$L_{up} = \alpha x_{up}^1 + \beta x_{up}^2 + \gamma x_{up}^3;$$

$$L_{down} = \alpha x_{down}^1 + \beta x_{down}^2 + \gamma x_{down}^3;$$

where $L_{up}$ represents the filtering upper limit value, $L_{down}$ represents the filtering lower limit value, $$x_{up}^1 \text{ and } x_{down}^1$$

respectively represent an upper limit value and a lower limit value of the wavelength range of ambient light acquired from dark environment, $$x_{up}^2 \text{ and } x_{down}^2$$

respectively represent an upper limit value and a lower limit value of the wavelength range of ambient light acquired from outdoor, $$x_{up}^3 \text{ and } x_{down}^3$$

respectively represent an upper limit value and a lower limit value of the wavelength range of ambient light acquired from indoor, while α, β and γ respectively represent weighting parameters corresponding to the wavelength ranges of ambient light acquired from dark environment, the wavelength ranges of ambient light acquired from outdoor, and the wavelength ranges of ambient light acquired from indoor.

In some other embodiments of the present disclosure, in the step of obtaining a filtering upper limit value based on the plurality of upper limit values, obtaining a filtering lower limit value based on the plurality of lower limit values, a minimum lower limit value among the plurality of lower limit values may be defined as the filtering lower limit value, and a maximum upper limit value among the plurality of upper limit values may be defined as the filtering upper limit value.

In some embodiments of the present disclosure, in the step of re-filtering the second wavelength range based on the filtering wavelength range to obtain a target filtering range, a wavelength range belonging to the filtering wavelength range is accessed from the second wavelength range as the target filtering range.

In some embodiments of the present disclosure, in the step of filtering the optical signals to be processed with the target filtering range to filter out ambient light from the optical signals to be processed, optical signals with wavelength range being the target filtering range is filtered out from the optical signals to be processed. In the present solution, the wavelength ranges of ambient light may be accurately calculated through the measured wavelength ranges of the plurality of groups of ambient light, the wavelength ranges belonging to the filtering wavelength range may be accessed from the second wavelength range in a subsequent step, to accurately determine a target filtering range of ambient light, and then the target filtering range is filtered out from the optical signals to be processed, which firstly avoids excessive filtering which results in the removal of part of red light, and on the other hand also accurately filters out ambient light.

The above-mentioned optical signal processing method may be applied to devices using fNIRS technology, PPG measurement technology and other physiological parameter detection based on infrared or near-infrared optical signals. For example, the above-mentioned method may be applied to an existing blood pressure acquisition apparatus based on photo-plethysmography, to achieve a more accurate measurement of blood pressure.

In an embodiment of the present disclosure, in addition to filtering out ambient light by using the above-mentioned optical signal processing method, the blood pressure measurement apparatus and the corresponding blood pressure measurement method may be further improved, by which more accurate continuous blood pressure values may be obtained by training a continuous blood pressure measurement model, acquiring photo-plethysmography signal data, and inputting the acquired photo-plethysmography signal data into the trained continuous blood pressure measurement model. Thus, not only a continuous blood pressure measurement may be performed, but also the accuracy and speed of the blood pressure measurement may be further improved.

As an example, where the optical signal processing method is further used for continuous blood pressure measurement and the continuous blood pressure measurement steps are improved, the optical signal processing method may further include:

- acquiring photo-plethysmography signal data a from the optical signals to be processed after filtering out ambient light;
- inputting the photo-plethysmography signal data into a pre-trained continuous blood pressure measurement model to obtain continuous blood pressure values, by which the pre-trained continuous blood pressure measurement model is obtained by a training based on following steps:
- acquiring the photo-plethysmography signal data from the signals to be processed after filtering out ambient light and normal arterial blood pressure waveform data;
- processing the photo-plethysmography signal data and the normal arterial blood pressure waveform data according to a pre-set data processing method to obtain a training sample; and
- performing the training using the training sample based on a convolutional neural network to obtain the continuous blood pressure measurement model.

By the continuous blood pressure measurement realized by the above-mentioned steps, not only the interference of ambient light is filtered out, but also a pre-trained continuous blood pressure measurement model with higher accuracy is adopted, which greatly improves the accuracy rate of blood pressure detection.

The continuous blood pressure measurement method and the corresponding apparatus according to an embodiment of the present disclosure will be described below.

The continuous blood pressure measurement method of the present disclosure is realized based on the pre-trained continuous blood pressure measurement model, and more specifically, by which after acquiring the photo-plethysmography signal data, the acquired photo-plethysmography signal data is input into the pre-trained continuous blood pressure measurement model to obtain continuous blood pressure values. The pre-trained continuous blood pressure measurement model is obtained based on the following training method.

Figure 3:
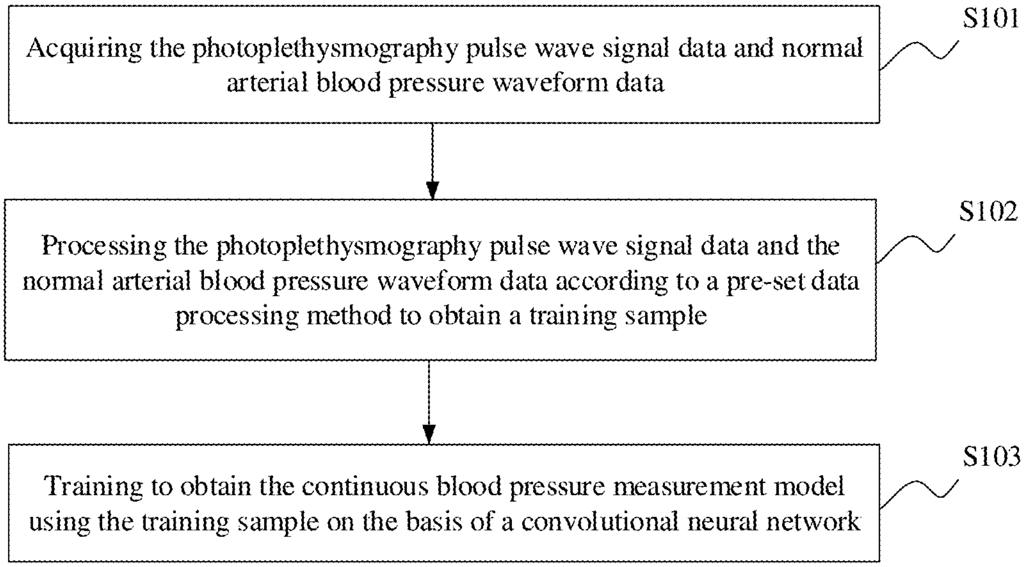
FIG. 3 is a flowchart of a training method for continuous blood pressure measurement model according to an embodiment of the present disclosure.

FIG. 3 is a flowchart of a training method for continuous blood pressure measurement model according to an embodiment of the present disclosure. Specifically, as shown in FIG. 3, the method includes:

Step S101, acquiring photo-plethysmography (PPG) signal data and normal arterial blood pressure (ABP) waveform data.

Optionally, the photo-plethysmography signal data may be acquired by a continuous blood pressure acquisition apparatus and the normal arterial blood pressure waveform data corresponding thereto may be acquired. In addition, the photo-plethysmography signal data acquired in this step may be the photo-plethysmography signal data, which is acquired by the continuous blood pressure acquisition apparatus and is obtained after ambient light is filtered out by the optical signal processing method as previously described.

Optionally, a large amount of photo-plethysmography signal data and normal arterial blood pressure waveform data needs to be acquired to ensure that a sufficient amount of training samples may be obtained by data pre-processing.

Step S102, processing the photo-plethysmography signal data and the normal arterial blood pressure waveform data according to the pre-set data processing method to obtain a training sample.

Optionally, the step of processing the photo-plethysmography signal data and the normal arterial blood pressure waveform data according to the pre-set data processing method to obtain a training sample includes:

- deleting photo-plethysmography signal data and normal arterial blood pressure waveform data that are less than a length threshold;
- filtering out photo-plethysmography signal data and normal arterial blood pressure waveform data that are not within a pre-set frequency band with a Butterworth bandpass filter;
- filtering the photo-plethysmography signal data and the normal arterial blood pressure waveform data with a Hampel filter to remove outliers;
- dividing the photo-plethysmography signal data and the normal arterial blood pressure waveform data in cycles, and deleting a flat line or a flat peak in the cycles; and
- deleting a cycle with a ratio of the flat line and the flat peak greater than a ratio threshold.

Illustratively, a minimum length required for the photo-plethysmography and normal arterial blood pressure may be set to 10 minutes. All data less than 10 minutes in length is deleted. It is ensured that changes in systolic and diastolic blood pressure may be contained.

The photo-plethysmography signal is then z-score normalized and filtered with a 4th order Butterworth bandpass filter with cut-off frequencies of 0.5 Hz and 8 Hz, respectively. Here, those below 0.5 Hz are considered as baseline oscillations and those above 8 Hz are high frequency noise. Then a Hampel filter is used to filter the signals to remove outliers. This requires a sliding window (data window with 8 seconds) containing 7 subsequent photo-plethysmography samples, and the median of this window is calculated. The standard deviation of each sample with respect to the window median is estimated, and if the sample differs from the window median by more than three standard deviations, the median is used to replace the sample.

Further, the signals are divided in cycles, with each cycle corresponding to one heartbeat. Flat lines and flat peaks in each cycle are deleted. If more than 5% of the cycle has a flat peak value, or more than 10% of recording duration is composed of flat line, the cycle or the recording is deleted.

Optionally, the step of processing the photo-plethysmography signal data and the normal arterial blood pressure waveform data according to the pre-set data processing method to obtain a training sample further includes:

intercepting two corresponding short segments of a normal arterial blood pressure waveform in proximity to the cycles of the photo-plethysmography signal data; and calculating an average peak value of peak values and an average valley value of valley values in the normal arterial blood pressure waveform of the two short segments;

where the average peak value is defined as systolic blood pressure, the average valley value is defined as diastolic blood pressure.

The obtained systolic blood pressure and diastolic blood pressure may be used as a label of the training sample.

Step S103, performing a training to obtain the continuous blood pressure measurement model with the training sample based on a convolutional neural network.

Illustratively, photo-plethysmography signal data for 8 seconds are sequentially intercepted as a group in steps of 2 seconds, and multiplied by the sampling rate with the data length to obtain an 8f vector, where f is the sampling rate.

Illustratively, CNN convolutional neural networks, cyclic neural networks, and RNN may be used for training to analyze time sequence.

The convolutional neural network includes an initial layer of a convolution filter (a vector box having a specific size), an activation function, a normalization layer, a maximum pooling layer, and a dropout layer.

The filter is a one-dimensional filter with a size of 8, a maximum pool size of the pooling layer may be set to 4, the dropout layer is a probability mask, a part of nodes will be blocked each time the gradient is updated, and the probability is taken to 0.1.

Illustratively, the continuous blood pressure measurement model may be trained in the python environment, and implemented using keras and TensorFlow backend.

In the training method for continuous blood pressure measurement model provided by an embodiment of the present disclosure, firstly the photo-plethysmography signal data and normal arterial blood pressure waveform data are acquired; then the photo-plethysmography signal data and the normal arterial blood pressure waveform data are processed according to the pre-set data processing method to obtain a training sample; and a training is performed using the training sample based on a convolutional neural network to obtain the continuous blood pressure measurement model. The present disclosure enables a continuous blood pressure measurement and improves the accuracy and speed of blood pressure measurement.

Figure 4:
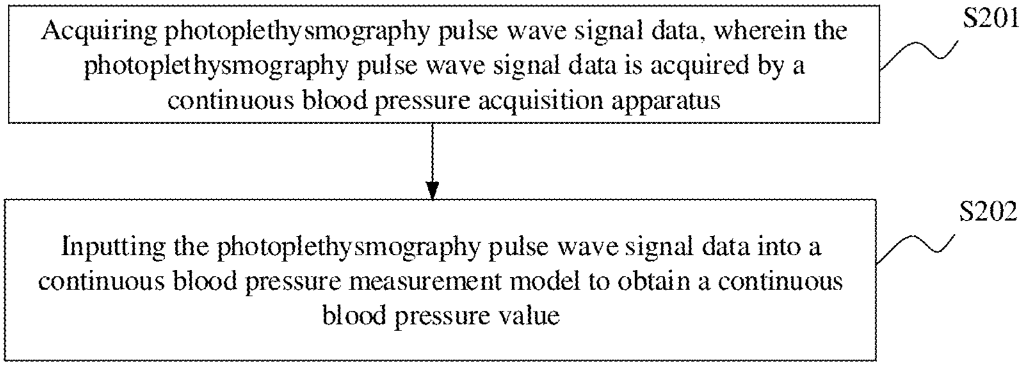
FIG. 4 is a flowchart of a continuous blood pressure measurement method according to an embodiment of the present disclosure.

FIG. 4 is a flowchart of a continuous blood pressure measurement method according to an embodiment of the present disclosure. As shown in FIG. 4, the method includes:

Step S201, acquiring photo-plethysmography signal data.

The photo-plethysmography signal data may be acquired by a continuous blood pressure acquisition apparatus. Preferably, the photo-plethysmography signal data acquired in this step may be the photo-plethysmography signal data, which is acquired by the continuous blood pressure acquisition apparatus and is acquired after ambient light if filtered out by the optical signal processing method as previously described.

Optionally, the continuous blood pressure acquisition apparatus includes at least one eight-channel light source for main light source projection and at least one photosensitive diode for receiving data from a multi-channel light source.

Optionally, the continuous blood pressure acquisition apparatus includes a wristband, the wristband is designed in a traditional blood pressure measurement manner. The wristband is designed to have a rectangular air bag, and an integrated air pressure sensing apparatus is provided inside the wristwatch, so as to carry out a traditional blood pressure measurement in cooperation with the photo-plethysmography detected by IR and red light.

Step S202, inputting the photo-plethysmography signal data into the trained continuous blood pressure measurement model to obtain continuous blood pressure values.

Illustratively, the photo-plethysmography signal data measured by the continuous blood pressure acquisition apparatus is input into the trained continuous blood pressure measurement model that outputs continuous blood pressure values measured according to the photo-plethysmography signal data.

Optionally, the continuous blood pressure measurement method further includes:

calculating a standard deviation from the continuous blood pressure values and a standard blood pressure value, where the standard blood pressure value is an average value of a plurality of blood pressure measurement values; and repeating the blood pressure measurement if the standard deviation is greater than a standard deviation threshold.

Illustratively, a build-in blood pressure measurement system with air pump of the continuous blood pressure acquisition apparatus may be used, and a blood pressure gauge with medical certification may also be used to perform a standard blood pressure data acquisition, to acquire a plurality of groups of blood pressure data and to calculate the mean value to obtain a standard blood pressure basic value: BP Criteria.

Illustratively, before the model outputs the continuous blood pressure values, the output data is evaluated to ensure the validity and reliability of the data, and if the setting condition is not satisfied, the blood pressure measurement in the present period is restarted. The standard error may be set as a maximum of 8 mmHg, for example, the default standard error is 5 mmHg. The error may be set as required to ensure the validity of the data.

For example, the evaluation formula is as follows:

$$M_{estimated\ error} = \frac{\sum_{i=1}^{n} (BP_{calculation} - BP_{standard})}{n};$$

$$M_{standard\ deviation} = \sqrt{\frac{\sum_{i=1}^{n} ((BP_{calculation} - BP_{standard}) - M_{estimated\ error})}{n-1}};$$

where, $BP_{calculation}$ is a blood pressure value measured and calculated by the model, $BP_{standard}$ is a blood pressure value obtained by a traditional measurement, $M_{estimated\ error}$ is the calculation error of model, $M_{standard\ deviation}$ is used to be compared with the set standard deviation, if it is greater than the set standard deviation, the blood pressure measurement shall be performed again.

By the continuous blood pressure measurement method provided by the embodiment of the present disclosure, firstly the photo-plethysmography signal data is acquired by a continuous blood pressure acquisition apparatus, the photo-plethysmography signal data is then input into the continuous blood pressure measurement model to obtain continuous blood pressure values. The present disclosure enables a continuous blood pressure measurement and improves the accuracy and speed of blood pressure measurement.

Figure 2:
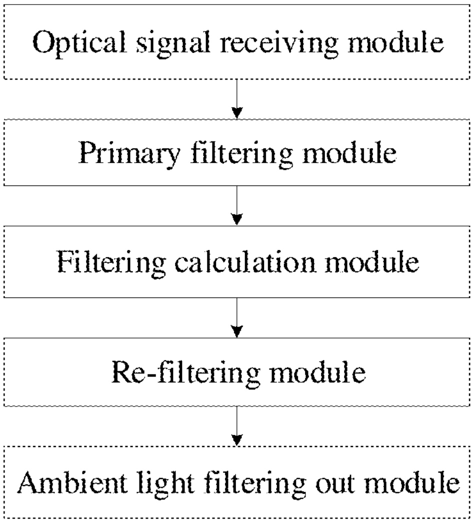
FIG. 2 is a schematic structural view of an optical signal processing system according to an embodiment of the present disclosure.

In accordance with the foregoing optical signal processing method, the present disclosure also provides an optical signal processing system, as shown in FIG. 2, including:

- an optical signal receiving module configured to access an optical signal to be processed through a spectrum analyzer, and the spectrum analyzer outputs a first wavelength range of the optical signal to be processed;
- a primary filter module configured to primarily filter the first wavelength range based on a pre-set wavelength threshold of red light to obtain a second wavelength range;
- a calculation module of filtration configured to acquire wavelength ranges of a plurality of groups of ambient light acquired in advance, to respectively acquire a plurality of upper limit values and a plurality of lower limit values of the wavelength ranges of the plurality of groups of ambient light, to obtain a filtering upper limit value by means of a weighted calculation based of the plurality of upper limit values and a filtering lower limit value by means of a weighted calculation based on the plurality of lower limit values, and to set a filtering wavelength range based on the filtering upper limit value and the filtering lower limit value;
- a re-filter module configured to re-filter the second wavelength range based on the filtering wavelength range to obtain a target filtering range; and
- an ambient light filtering out module configured to filter the optical signals to be processed with the target filtering range to filter out ambient light from the optical signals to be processed.

By the system of the above-mentioned solution, the optical signals to be processed is primarily filtered by means of the wavelength of red light, then the plurality of groups of ambient light acquired in advance is re-filtered to obtain the target wavelength range of ambient light to be filtered out, a filter is used to filter out the target wavelength range from the optical signals to be processed so as to filter out ambient light from the optical signals to be processed. This system may achieve a more accurate ambient light filtering and make the optical signal acquisition more accurate.

In some embodiments of the present disclosure, the processing step of the calculation module of filtration includes: respectively accessing an upper limit value and a lower limit value of the wavelength range of each acquired ambient light, if the wavelength ranges of the plurality of groups of ambient light include wavelength ranges of ambient light acquired from dark environment, wavelength ranges of ambient light acquired from outdoor, and wavelength ranges of ambient light acquired from indoor.

In some embodiments of the present disclosure, the processing step of the calculation module of filtration further includes: if the wavelength ranges of the plurality of groups of ambient light include the wavelength ranges of ambient light acquired from dark environment, the wavelength ranges of ambient light acquired from outdoor and the wavelength ranges of ambient light acquired from indoor, respectively determining weighting parameters corresponding to the wavelength ranges of ambient light acquired from dark environment, the wavelength ranges of ambient light acquired from outdoor and the wavelength range of ambient light acquired from indoor, calculating a weighted average value of the plurality of upper limit values and that of the plurality of lower limit values based on the weighting parameters to obtain a filtering upper limit value and a filtering lower limit value.

An apparatus configured to perform the above-described training method for continuous blood pressure measurement model according to an embodiment of the present application will be described in detail with reference to FIG. 5.

Figure 5:
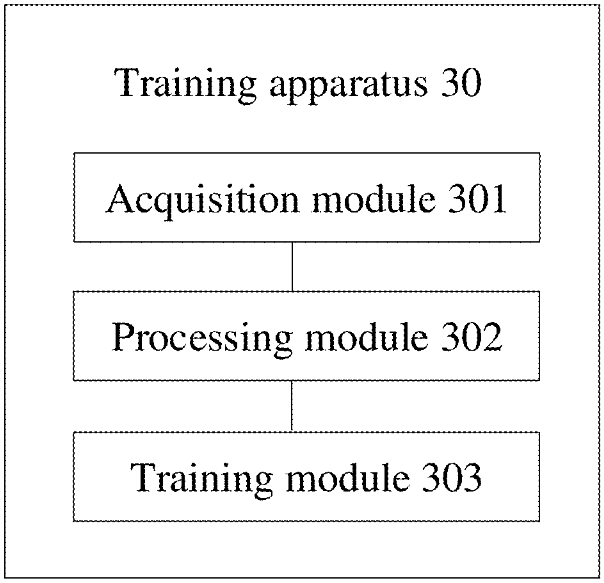
FIG. 5 is a structural schematic view of a training apparatus for continuous blood pressure measurement model according to an embodiment of the present disclosure.

Illustratively, FIG. 5 is a schematic view showing the structure of a training apparatus for continuous blood pressure measurement model according to an embodiment of the present disclosure. As shown in FIG. 5, the training apparatus 30 includes:

- an acquisition module 301 configured to acquire photo-plethysmography signal data and normal arterial blood pressure waveform data;
- a processing module 302 configured to process the photo-plethysmography signal data and the normal arterial blood pressure waveform data according to a pre-set data processing method to obtain a training sample; and
- a training module 303 configured to perform a training using the training sample based on a convolutional neural network to obtain the continuous blood pressure measurement model.

Optionally, the processing module 302 is further configured to delete the photo-plethysmography signal data and the normal arterial blood pressure waveform data that are less than a length threshold, to filter out the photo-plethysmography signal data and the normal arterial blood pressure waveform data that are not within a pre-set frequency band with a Butterworth bandpass filter, to filter the photo-plethysmography signal data and the normal arterial blood pressure waveform data with a Hampel filter to remove outliers, to divide the photo-plethysmography signal data and the normal arterial blood pressure waveform data in cycles and delete flat lines or flat peaks appearing in the cycles, and to delete a cycle if a ratio of the flat line and the flat peak in the cycle is greater than a ratio threshold.

Optionally, the processing module 302 is further configured to intercept two corresponding short segments of a normal arterial blood pressure waveform in proximity to cycles of the photo-plethysmography signal data, to calculate an average peak value of peak values and an average valley value of valley values in the normal arterial blood pressure waveform of the two short segments, where the average peak value is defined as systolic blood pressure, and the average valley value is defined as diastolic blood pressure.

Figure 6:
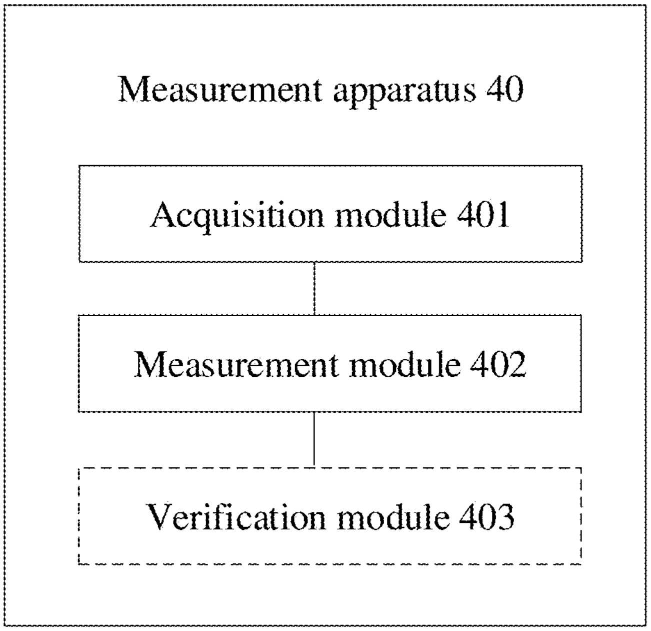
FIG. 6 is a structural schematic view of a continuous blood pressure measurement apparatus according to an embodiment of the present disclosure.

An apparatus configured to perform the above-described continuous blood pressure measurement method according to an embodiment of the present application will be described in detail with reference to FIG. 6. Illustratively, FIG. 6 is a schematic structural view of the continuous blood pressure measurement apparatus according to the embodiment of the present disclosure. As shown in FIG. 6, the measurement apparatus 40 includes:

- an acquisition module 401 configured to acquire photo-plethysmography signal data,
- where, the photo-plethysmography signal data is acquired by a continuous blood pressure acquisition apparatus;

a measurement module 402 configured to input the photo-plethysmography signal data into a continuous blood pressure measurement model to obtain continuous blood pressure values.

Optionally, the continuous blood pressure acquisition apparatus includes at least one eight-channel light source for main light source projection and at least one photosensitive diode for receiving data from a multi-channel light source.

Optionally, the apparatus further includes a verification module 403 configured to calculate a standard deviation from the continuous blood pressure values and a standard blood pressure value, and to repeat the blood pressure measurement if the standard deviation is greater than a standard deviation threshold. The standard blood pressure value is an average value of a plurality of blood pressure measurement values.

The disclosure also provides an electronic device, such as an optical signal processing apparatus, including a computer device including a processor and a memory, computer instructions are stored in the memory, the processor is adapted to execute the computer instructions stored in the memory, and when the processor executes the computer instructions, the electronic device implements the steps of the optical signal processing method and/or the continuous blood pressure measurement method as described above.

In another aspect of the present disclosure, there is also provided a computer-readable storage medium storing one or more programs used by one or more processors to perform the steps of the optical signal processing method and/or the continuous blood pressure measurement method of the present disclosure.

Figure 7:
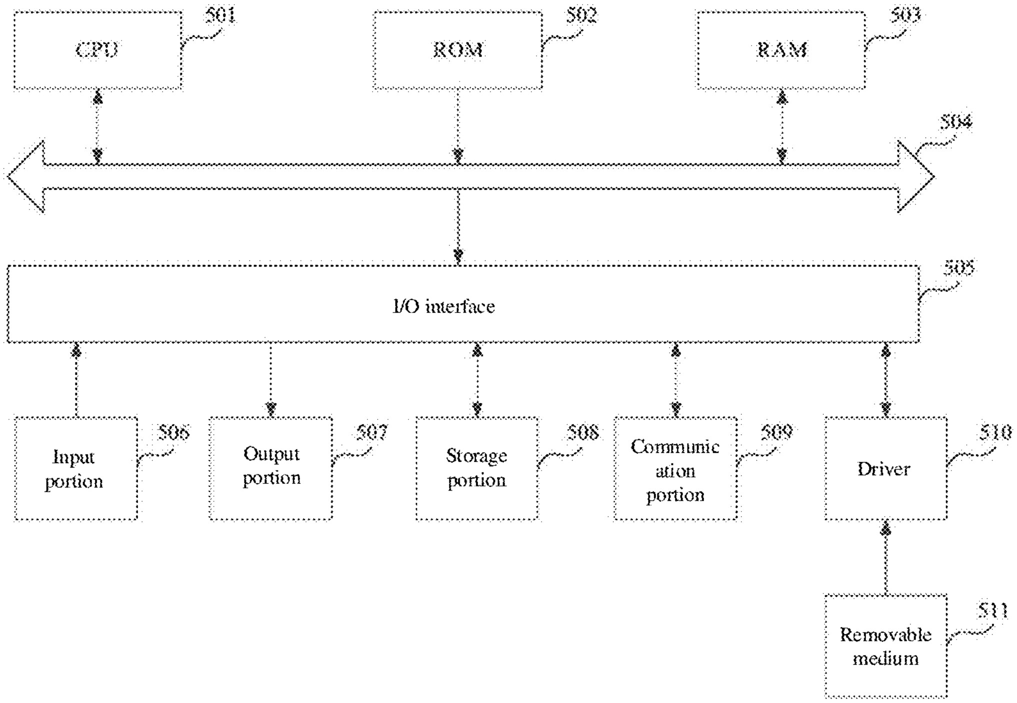
FIG. 7 is a structural view of an electronic device according to an embodiment of the present disclosure.

Embodiments of the present disclosure also provide an example of a computer electronic device. FIG. 7 shows a schematic structural view of an electronic device according to an embodiment of the present disclosure. As shown in FIG. 7, the computer electronic device includes a central processing unit (CPU) 501 which may execute various appropriate actions and processes according to a program stored in a read-only memory (ROM) 502 or a program loaded from a storage portion 508 into a random access memory (RAM) 503. In the RAM 503, various programs and data required for the operation of the system are also stored. The CPU 501, the ROM 502 and the RAM 503 are connected to each other via a bus 504. An input/output (I/O) interface 505 is also connected to the bus 504.

The following components are connected to the I/O interface 505: an input portion 506 including a keyboard, a mouse, etc., an output portion 507 such as a cathode ray tube (CRT), a liquid crystal display (LCD), etc. and a speaker, etc., a storage portion 508 including a hard disk, etc., and a communication portion 509 including a network interface card such as a LAN card, a modem, etc. The communication portion 509 performs a communication processing via a network such as the internet. A driver 510 is also connected to the I/O interface 505 as required. A removable medium 511, such as a magnetic disk, optical disk, magneto-optical disk, semiconductor memory or the like, is mounted on the driver 510 as required, so that a computer program read therefrom is mounted into the storage portion 508 as required.

The flowcharts and block diagrams in the figures illustrate the architecture, functionality, and operation, which may be realized by systems, methods, and computer program products according to various embodiments of the present disclosure. In this regard, each block in the flowcharts or block diagrams may represent a module, a segment, or a portion of code, which includes one or more executable instructions for implementing the specified logical function(s). It should also be noted that in some alternative implementations, the functions noted in the blocks may occur out of the order noted in the figures. For example, two blocks shown in succession may, in fact, be executed substantially in parallel, and sometimes in the reverse order, depending upon the functionality involved. It will also be noted that each block of the block diagrams and/or flowchart illustrations, and combinations of blocks in the block diagrams and/or flowchart illustrations, may be implemented by dedicated hardware-based systems which perform the specified functions or operations, or by combinations of dedicated hardware and computer instructions.

Modules or the modules described in connection with the embodiments of the disclosure may be implemented in software or in hardware. The described module or modules may also be provided in a processor, for example, as follows: a processor includes an acquisition module 301, a processing module 302 and a training module 303, by which the names of these modules do not constitute a limitation on the module itself under certain circumstances. For example, the acquisition module 301 may also be described as "an acquisition module 301 for acquiring photo-plethysmography signal data and normal arterial blood pressure waveform data".

In another aspect of the present disclosure, there is also provided a computer-readable storage medium, which may be a computer-readable storage medium contained in the training apparatus for continuous blood pressure measurement model or the continuous blood pressure measurement apparatus described in the above-mentioned embodiment, which may also be a computer-readable storage medium that exists separately and is not assembled into an electronic device. The computer-readable storage medium stores one or more programs used by one or more processors to perform the training method for continuous blood pressure measurement model or the continuous blood pressure measurement method described in the present disclosure.

The computer-readable storage medium of the present disclosure may be a tangible storage medium such as a random access memory (RAM), a memory, a read only memory (ROM), an electrically programmable ROM, an electrically erasable programmable ROM, a register, a floppy disk, a hard disk, a removable storage disk, a CD-ROM, or any other form of storage medium known in the art.

A person skilled in the art should understand that the various exemplary components, systems, and methods described in conjunction with the embodiments disclosed herein may be implemented in hardware, software, or a combination of both. Whether these functions are realized by hardware or software depends on specific applications and design constraints of technical solutions. The skilled in the art may adopt different methods to realize the described functions regarding to each specific application, which, however, should be considered as falling within the scope of the present disclosure. When implemented in hardware, it may be, for example, an electronic circuit, an application specific integrated circuit (ASIC), appropriate firmware, a plug-in, a function card, or the like. When implemented in software, the elements of the disclosure are programs or code segments that are used to perform the required tasks. The program or code segments may be stored in a machine-readable medium or transmitted over a transmission medium or communication link by a data signal embodied in a carrier wave.

It should be understood that the disclosure is not limited to the particular arrangements and processes described above and illustrated in the drawings. A detailed description of known methods is omitted herein for the sake of brevity. In the above-mentioned embodiments, several specific steps have been described and shown as examples. However, the method processes of the present disclosure are not limited to the specific steps described and illustrated, and a person skilled in the art may make various changes, modifications and additions, or change the order between the steps, after understanding the spirit of the present disclosure.

Features that are described and/or illustrated with respect to one embodiment of the disclosure may be used in the same way or in a similar way in one or more other embodiments and/or in combination with or instead of the features of the other embodiments.

The foregoing is merely preferred embodiments of the present disclosure, and is not intended to limit the present disclosure, it will be understood by those having ordinary skill in the art that various changes may be made of the embodiments of the present disclosure. Thus, it is intended that the scope of protection of the present disclosure cover the modifications, equivalents, and improvements falling within the spirit and principle of the present disclosure.

What is claimed is:

1. An optical signal processing method, comprising:

receiving optical signals to be processed by a spectrum analyzer, and outputting a first wavelength range of the optical signals to be processed by the spectrum analyzer, primary filtering the first wavelength range based on a pre-set wavelength threshold of red light to obtain a second wavelength range by filtering out wavelength ranges higher than the pre-set wavelength threshold of red light, accessing wavelength ranges of a plurality of groups of ambient light acquired in advance, wherein the wavelength ranges of the plurality of groups of ambient light comprise wavelength ranges of ambient light acquired from a dark environment, wavelength ranges of ambient light acquired from outdoor, and wavelength ranges of ambient light acquired from indoor, respectively accessing a plurality of upper limit values and a plurality of lower limit values of the wavelength ranges of the plurality of groups of ambient light, respectively determining weighting parameters corresponding to the wavelength ranges of the plurality of groups of ambient light, and calculating a weighted average value of the plurality of upper limit values and a weighted average value of the plurality of lower limit values based on the weighting parameters to obtain a filtering upper limit value based on the plurality of upper limit values and to obtain a filtering lower limit value based on the plurality of lower limit values, and setting a filtering wavelength range based on the filtering upper limit value and the filtering lower limit value, re-filtering the second wavelength range based on the filtering wavelength range to obtain a target filtering range of ambient light wavelengths, and filtering the optical signals to be processed with the target filtering range to filter out ambient light from the optical signals to be processed.

2. The optical signal processing method according to claim 1, wherein primary filtering the first wavelength range based on the pre-set wavelength threshold of red light to obtain the second wavelength range comprises at least one of: obtaining a wavelength range of red light, wherein a lower limit value of the wavelength range of red light is defined as a wavelength threshold of red light, and filtering out wavelength ranges higher than the wavelength threshold of red light from the first wavelength range to obtain the second wavelength range.

3. The optical signal processing method according to claim 1, wherein obtaining the filtering upper limit value based of the plurality of upper limit values, and obtaining the filtering lower limit value based on the plurality of lower limit values comprises: defining a minimum lower limit value among the plurality of lower limit values as the filtering lower limit value and a maximum upper limit value among the plurality of upper limit values as the filtering upper limit value.

4. The optical signal processing method according to claim 1, wherein re-filtering the second wavelength range based on the filtering wavelength range to obtain the target filtering range comprises: accessing a wavelength range belonging to the filtering wavelength range from the second wavelength range as the target filtering range.

5. The optical signal processing method according to claim 1, wherein filtering the optical signals to be processed with the target filtering range to filter out the ambient light from the optical signals to be processed comprises: filtering the optical signals to be processed with the target filtering range, and filtering out optical signals with a wavelength range being within the target filtering range from the optical signals to be processed.

6. The optical signal processing method according to claim 1, wherein the optical signal processing method is configured to perform a continuous blood pressure measurement and further comprises:

acquiring photo-plethysmography signal data from the optical signals to be processed after filtering out the ambient light, and inputting the photo-plethysmography signal data into a pre-trained continuous blood pressure measurement model to obtain continuous blood pressure values, wherein the pre-trained continuous blood pressure measurement model is obtained by training based on following steps:

acquiring the photo-plethysmography signal data from the optical signals to be processed after filtering out the ambient light and normal arterial blood pressure waveform data, processing the photo-plethysmography signal data and the normal arterial blood pressure waveform data according to a pre-set data processing method to obtain a training sample, and performing the training using the training sample based on a convolutional neural network to obtain the pre-trained continuous blood pressure measurement model.

7. The optical signal processing method according to claim 6, further comprising:

calculating a standard deviation according to the continuous blood pressure values and a standard blood pressure value, wherein the standard blood pressure value is an average value of a plurality of blood pressure measurement values; and repeating a blood pressure measurement when the standard deviation is greater than a standard deviation threshold.

8. The optical signal processing method according to claim 6, wherein processing the photo-plethysmography signal data and the normal arterial blood pressure waveform data according to the pre-set data processing method to obtain the training sample comprises:

deleting photo-plethysmography signal data and normal arterial blood pressure waveform data that are less than a length threshold, filtering out photo-plethysmography signal data and normal arterial blood pressure waveform data that are not within a pre-set frequency band with a Butterworth bandpass filter, filtering the photo-plethysmography signal data and the normal arterial blood pressure waveform data with a Hampel filter to remove outliers, dividing the photo-plethysmography signal data and the normal arterial blood pressure waveform data in cycles, and deleting flat lines or flat peaks in the cycles, and deleting a cycle with a ratio of flat lines and flat peaks greater than a ratio threshold.

9. The optical signal processing method according to claim 6, wherein processing the photo-plethysmography signal data and the normal arterial blood pressure waveform data according to the pre-set data processing method to obtain the training sample further comprises:

intercepting two corresponding short segments of normal arterial blood pressure waveform in proximity to cycles of the photo-plethysmography signal data, and calculating an average peak value of peak values and an average valley value of valley values in the two corresponding short segments of normal arterial blood pressure waveform, wherein the average peak value is defined as a systolic blood pressure, the average valley value is defined as a diastolic blood pressure, and the systolic blood pressure and the diastolic blood pressure are defined as labels of the training sample.

10. The optical signal processing method according to claim 6, wherein the optical signals to be processed are acquired by a continuous blood pressure acquisition apparatus comprising at least one eight-channel light source for main light source projection and at least one photosensitive diode for receiving data from a multi-channel light source.

11. An optical signal processing system configured to be applied to the optical signal processing method according to claim 1, comprising:

the spectrum analyzer configured to receive the optical signals to be processed and output the first wavelength range of the optical signals to be processed;

a processor; and a memory storing executable instructions that, when executed by the processor, cause the optical signal processing system to implement functional modules including:

an optical signal receiving module configured to access the optical signals to be processed through the spectrum analyzer, wherein the spectrum analyzer outputs the first wavelength range of the optical signals to be processed, a primary filter module configured to primarily filter the first wavelength range based on the pre-set wavelength threshold of red light to obtain the second wavelength range by filtering out the wavelength ranges higher than the pre-set wavelength threshold of red light, a calculation module of filtration configured to access the wavelength ranges of the plurality of groups of ambient light acquired in advance, to respectively access the plurality of upper limit values and the plurality of lower limit values of the wavelength ranges of the plurality of groups of ambient light, to respectively determine weighting parameters corresponding to the wavelength ranges of the plurality of groups of ambient light, and calculate a weighted average value of the plurality of upper limit values and a weighted average value of the plurality of lower limit values based on the weighting parameters to obtain the filtering upper limit value based on the plurality of upper limit values and the filtering lower limit value based on the plurality of lower limit values, and to set the filtering wavelength range based on the filtering upper limit value and the filtering lower limit value, a re-filter module configured to re-filter the second wavelength range based on the filtering wavelength range to obtain the target filtering range of ambient light wavelengths, and an ambient light filtering out module configured to filter the optical signals to be processed with the target filtering range to filter out the ambient light from the optical signals to be processed.

12. The optical signal processing system according to claim 11, further comprising:

a continuous blood pressure measurement module configured to acquire photo-plethysmography signal data from the optical signals to be processed after filtering out the ambient light, and to input the photo-plethysmography signal data into a continuous blood pressure measurement model to obtain continuous blood pressure values.

13. The optical signal processing system according to claim 12, further comprising:

a training module for continuous blood pressure measurement model configured to acquire the photo-plethysmography signal data from the optical signals to be processed after filtering out the ambient light and normal arterial blood pressure waveform data, to process the photo-plethysmography signal data and the normal arterial blood pressure waveform data according to a pre-set data processing method to obtain a training sample, and to perform training using the training sample based on a convolutional neural network to obtain the continuous blood pressure measurement model.

14. An electronic device, comprising a memory and a processor, wherein a computer program is stored in the memory, and the processor is configured to implement the optical signal processing method according to claim 1 when executing the computer program.

* * * * *